US009886561B2

(12) United States Patent
Hospodor et al.

(10) Patent No.: US 9,886,561 B2
(45) Date of Patent: Feb. 6, 2018

(54) EFFICIENT ENCODING AND STORAGE AND RETRIEVAL OF GENOMIC DATA (71) Applicant: The Regents of the University of California, Oakland, CA (US)

(72) Inventors: Andrew Hospodor, Santa Cruz, CA (US); Ignacio Corderi, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 346 days.

(21) Appl. No.: 14/625,967

(22) Filed: Feb. 19, 2015

(65) Prior Publication Data

US 2015/0248430 A1    Sep. 3, 2015

Related U.S. Application Data

(60) Provisional application No. 61/941,718, filed on Feb. 19, 2014.

(51) Int. Cl.
*G06F 19/00* (2011.01)

(52) U.S. Cl.
CPC .................. *G06F 19/70* (2013.01)

(58) Field of Classification Search
CPC .............. G06F 19/22; G06F 19/322
USPC .......... 707/692, 602, 693; 702/20
See application file for complete search history.

(56) References Cited

U.S. PATENT DOCUMENTS

| | | | |
|---|---|---|---|
| 2013/0166221 A1* | 6/2013 | Inglis | G06F 19/22 702/20 |
| 2014/0309944 A1* | 10/2014 | van Rooyen | G06F 19/22 702/20 |
| 2014/0337276 A1* | 11/2014 | Iordanov | G06F 9/4435 707/602 |

* cited by examiner

*Primary Examiner* — Hung T Vy
(74) *Attorney, Agent, or Firm* — Carter, DeLuca, Farrell & Schmidt, LLP (57) ABSTRACT

A new method for encoding genomic data that reduces storage footprint by two orders of magnitude while preserving acceptable quality data.

14 Claims, 5 Drawing Sheets

```
Ref data  :      ACCCTGTGCAACAACCCTGTGAACAGGT
Snippet 1:       ACCCTGTGCAACAA
Snippet 2:       ACCCTTTGCAAC
Snippet 3:       ACCCTGTGCAA
Snippet 4:         CCCTGTGCCACAACCC
Snippet 5:         CCCTGTGCCACAAC
Snippet 6:           CCTGTGCCA
Snippet 7:          CCTGTGCCACAACCCAGT
Snippet 8:             TGTGCAACAACCCAGTGAA
Snippet 9:             TGTGCAACAACCCAGTG
Snippet 10:            GTGCAACAACCCAGTGAACA
Snippet 11:             GCAACAACCCAGTGAAC
Snippet 12:              CAACAACCCAGTGAACAGGT + QUAL data for each nucleotide
+ Meta-data
```

```
Position         123456789 123456789 12345678
Ref data    :    ACCCTGTGCAACAACCCTGTGAACAGGT
Snippet  1:      ACCCTGTGCAACAA
Snippet  2:      ACCCTTGCAAC
Snippet  3:      ACCCTGTGCAA
Snippet  4:        CCCTGTGCCACAACCC
Snippet  5:        CCCTGTGCCACAAC
Snippet  6:         CCTGTGCCA
Snippet  7:         CCTGTGCCACAACCCAGT
Snippet  8:            TGTGCAACAACCCAGTGAA
Snippet  9:            TGTGCAACAACCCAGTG
Snippet 10:             GTGCAACAACCCAGTGAACA
Snippet 11:              GCAACAACCCAGTGAAC
Snippet 12:               CAACAACCCAGTGAACAGGT Position         123456789 123456789 12345678
Encoding    :    ACCCTGTGC*ACAACCCAGTGAACAGGT
Conflict File {10: Value C read 4 times, A
read 8 Times; 18: QUAL 3}
```

EFFICIENT ENCODING AND STORAGE AND RETRIEVAL OF GENOMIC DATA

RELATIONSHIP TO OTHER APPLICATIONS

This application claims priority to and the benefit of U.S. provisional patent application No. 61/941,718 titled EFFICIENT ENCODING AND STORAGE AND RETRIEVAL OF GENOMIC DATA filed 19 Feb. 2014. This application in incorporated by reference for all purposes.

GOVERNMENT FUNDING

This invention was made with government support under The Center for Research in Storage Systems (CRSS) NSF grant number is IIP-0934401. The government has certain rights in the invention.

SEQUENCE LISTING STATEMENT

No sequence listing statement is provided because the sequence data provided is solely illustrative of the invention and is not part of the invention or any claim.

FIELD OF THE INVENTION

The invention is directed towards encoding data, specifically genomic data, more specifically to efficient encoding, storage and retrieval of genomic data by removing data duplications. The invention also encompasses a computerized method of reducing genomic data set sizes having duplicated data into a reduced de-duplicated data set, and a DNA sequencing system for producing multiple DNA data segments and then efficiently encoding those data segments into de-duplicated machine and human readable formats.

A sequence listing text (.txt) file is submitted herewith under 37 CFR. 1.821(c) and is hereby incorporated by reference in its entirely. The details of the file as required under 37 CFR. 1.52(e)(5) and 37 CFR 1.77(b)(5) are as follows: Name of file is 2_SC2014_456_SeqList_ST25.txt; date of creation is May 8, 2015; size is 4 kilobytes. The content of the sequence listing information recorded in computer readable form is identical to the written sequence listing (if any) and identical to the sequence information provided with the original filed application and with the priority application, and contains no new matter.

BACKGROUND OF THE INVENTION

Genomic data is commonly stored in the .bam or .sam file format. The .sam format is a human readable text format for storing sequenced data in tab delimited ASCII columns. It is a human readable version of the .bam format which stores the same data in a compressed, indexed, binary form. Both formats represent aligned data for a sample along with both quality (QUAL) scores and metadata (Tags). The results of many small reads are aligned and stored along with their quality data stores. A typical whole genome sequence of a human we require approximately 300 GB of storage. In a large scale computing environment 300 GB .bam files can easily consume available storage and clog networks. Existing practice relies heavily compression using techniques such as lempil ziv and gziv. More recent techniques use standard reference genomes, such as HG19, compiled from a variety of human genomes. Quality scores are calculated in the standard manner by the sequencer, such an Illumina, MySeq etc. Quality scores are discussed in many publications including in the on-line publication from Illumina called "Understanding Illumina quality scores"; also see E. Green 1998 "Base-calling of automated sequencer traces using phred. II. Error probabilities"; Genome Research 8: 186-194.

The .sam (and .bam) file formats are well known, standardized, useful, but unfortunately require about 300-400 GB of storage per human sequence even after using compression techniques such as Lempil, Ziv or Gziv. That storage size is simply too large for many purposes, especially if all cancer patient genomic data is to be gathered, stored, and/or transmitted. Since processing cancer genomic data is best practiced in large scale computing environments storing 300 GB .bam files on thousands of cancer patients would easily consume all available storage and clog computer networks.

As an example of the required data sizes consider a rather small trial to correlate genetic mutations with a specific cancer, for example breast cancer, in the hopes of identifying an effective therapy. That trial may have 800 breast cancer patients with 3 to 4 sequences each and would require at least 1 PB of storage per patient. Genomic researchers need to reduce such capacity without loss of quality sequence data, without increased processing time associated with decompression, and without the excessive costs and delays currently associated with moving genomic data from one location to another. Complicating the matter are issues in the alignment of the segment snippet sequences which make existing methods of compression and de-duplication (removal of duplicated data) less effective.

As another example, if precision oncology becomes a reality "whole genome sequencing," particularly in clinical treatments of cancer, would rapidly consume all available storage unless an effective way of reducing the required data size is implemented. In 2010, 13 million Americans had cancer. With existing technology, a single whole genome sequence for every person would require 39 exabytes (39,000 petabytes, 39 million terabytes or 39 billion gigabytes). There simply isn't enough storage for that.

In view of the foregoing improved data encoding for genomic data would be useful. Beneficially such data encoding would be computer driven to eliminate redundant genomic data (de-duplication). Preferably such encoded data would be compressed and searchable. In addition it should merge re-reads of the same nucleotide into a single nucleotide having an averaged quality score. In practice, the improved data encoding should enable computer processing of the resulting encoded data without loss of information related to multiple nucleotides in sample segments. Ideally, the encoded data would be produced by a computerized DNA sequencing system that would provide encoded data that is so efficiently packed that it would allow individual cancer patients to store their genomic data on a memory stick or other computer readable memory, would enable faster transmissions of data, would require less data storage space, would support standardized data processing, and could enable improved data processing.

BRIEF SUMMARY OF THE INVENTION

The invention provides a new method for encoding genomic data that reduces storage footprint by two orders of magnitude while preserving acceptable quality data.

The invention encompasses a method that eliminates redundant genomic data. Genomic data is commonly stored in the .bam or .sam file formats. These formats often include re-reads of the same base pairs, resulting in redundant genomic data. Furthermore, each read includes associated quality scores and meta-data. The inventors reduced re-reads of the same base pair to a single nucleotide and average quality score. For base pairs where multiple nucleotides are present, we annotate on a separate conflict stream the number of reads for each nucleotide and the corresponding average quality. This encoding allows the user to establish a threshold for good data, and thereby eliminate noisy or bad data. Above this threshold, all data is preserved.

One embodiment of the invention allows the sharing of deduplication libraries. This promotes file sharing by passing references to redundant data in the deduplication library rather the data itself. In another embodiment the deduplication library may be organized as a collection of objects, each representing a gene found in the cancer genome atlas (TCGA).

The invention dynamically creates a deduplication library without the need of a standards body to decide what should be in the reference.

The method of the invention reduces the alignment information and reference differences to a single data stream storing only what is different from the reference. It then annotates conflict information on a separate file when there are multiple possible values on the same location.

Figure 1:
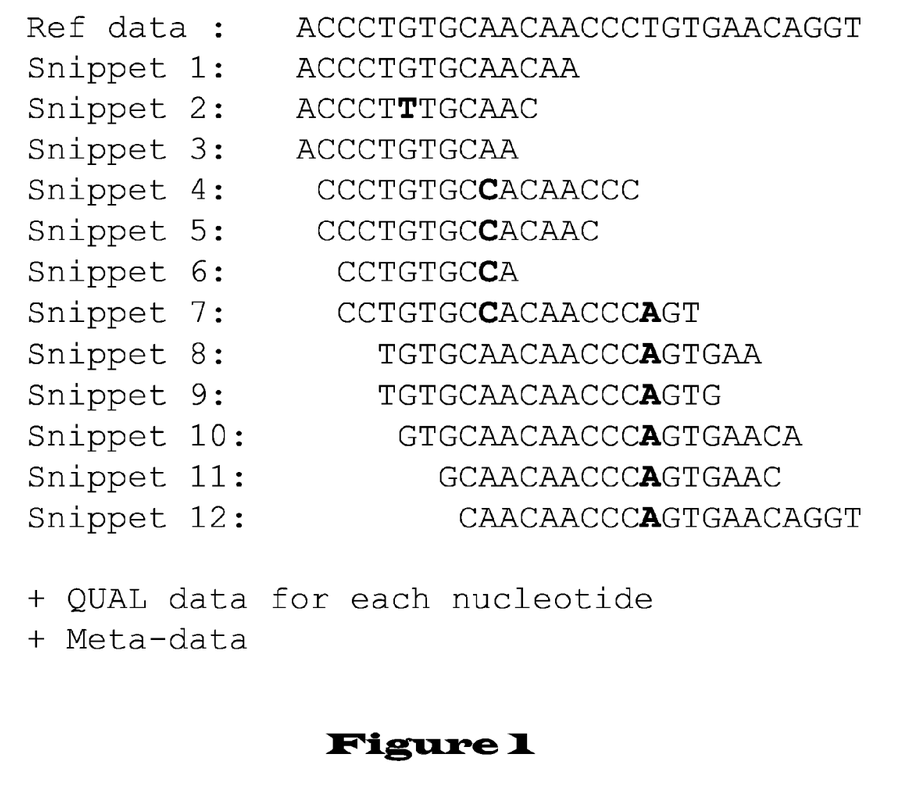
FIG. 1 is an illustration of a reference data set and nucleotide data obtained from multiple sequencing runs.

FIG. 1 illustrates a highly simplified genomic data set obtained by multiple DNA sequencing runs on a sample. Shown are run snippets (sequences) 1-12 which represent the results of the individual sequencing runs. Also shown in FIG. 1 is a ordered reference sequence which forms a "standard" nucleotide sequence that represents the normalized set of nucleotides in the population. As shown, the individual nucleotides of the snippets can be "aligned" with the reference sequence. Also shown in FIG. 1 is stored additional data that represents QUAL scores, which are the quality measurements of each nucleotide on each snippet as well as the quality of the mapping of each snippet (how well the base pair data align with other snippets). In addition FIG. 1 shows meta-data, which are mostly instructional data tags for machine processing such as data integer sizes, how it is specified (such as 32 bit signed integer data), aids in alignment, and user-defined information.

The present invention encompasses a computer implemented system that implements reduced size genomic data to produce encoded data that is compressed and contains de-duplicated data. That computer driven system encodes data by eliminating redundant genomic data by processing reads and re-reads of sample segments against a reference to produce a coalescent nucleotide result having an averaged quality score that is properly aligned in a data sequence. In practice the computer driven system produces encoded data supporting annotations in a separate conflict stream when multiple nucleotides are present in the samples. The encoded data enables faster transmissions of data, requires far less data storage space, supports standardized data processing and improves the speed of data processing.

The encoded data enables the user to establish a threshold for good data, thus helping eliminate noisy or bad data, while preserving all data above the threshold. In addition, the computer driven system is suitable for incorporating into a DNA sequencing system which produces the encoded data as an output.

The present invention includes the following embodiments:

A method for compressing genomic data, the method comprising the steps of: (i) providing a computer having a memory in functional communication with a processor; (ii) inputting multiple segments (multiple reads, polynucleotides) of genomic sequences and their quality scores into the computer memory; (iii) providing reference genomic data comprising a sequence of genomic data; (iv) accessing the reference genomic data; (v) aligning the multiple segments with the reference genomic data; (vi) comparing individual nucleotides in the aligned multiple segments using a processor; (vii) creating a de-duplicated sequence of encoded data aligned with the reference genomic data; wherein the encoded data contains the nucleotide label for agreed upon nucleotides at a particular nucleotide location.

In additional embodiments the method may further include the step of creating a conflict file for containing information regarding conflicts in the aligned multiple segments.

In an additional embodiment the method may further include the step of placing a quality score threshold in memory.

In an additional embodiment the method may further include the step of including the step of ignoring a nucleotide in the aligned multiple segments having a quality below the threshold.

In an additional embodiment the method may further include the step of selecting a nucleotide from conflicting nucleotides and inserting the selected nucleotide in the encoded data and inserting information regarding the conflicting nucleotides in the conflict file.

Another embodiment of the invention is a computer having a processer, a first memory, a second memory and an input port programmed to produce encoded genomic data, by performing the following steps: inputting multiple segments of genomic sequences and their qualities scores into the input port; storing the multiple segments of genomic sequences in the first memory; accessing and storing reference genomic data comprising a sequence of genomic data into the first memory; aligning the multiple segments of genomic sequences with the reference genomic data; locating a pointer at the first position of the reference data; (a) processing the first memory to compare individual nucleotides in the aligned multiple segments at the pointer position; processing the compared individual nucleotides to determine a culminate nucleotide from the individual nucleotides to be stored in an encoded data file at the pointer position; (b) determining if the pointer is at the last position of the reference data; if the pointer is at the last position of the reference data jumping to step (c); stepping the pointer to the next position of the reference data; returning to step (a); (c) storing the encoded data file as encoded genomic data in the second memory.

In an additional embodiment the computer-implemented method may further include the step of creating a conflict file in said second memory for containing information regarding conflicts in aligned nucleotides.

In an additional embodiment the computer-implemented method may further include the step of storing a quality score threshold in the first memory.

In an additional embodiment the computer-implemented method may further include the step of ignoring a nucleotide in an aligned multiple segment that has a quality below the threshold.

Another embodiment is a genomic sequencing system, comprising: a genomic sequencer for producing segments of DNA sequences having QUAL scores and meta-data; a computer having a processor, a first memory, a second memory, and an input port; a genomic buss connecting said genomic sequencer to said input port; wherein the computer interacts with the genomic sequencer to perform the following steps: inputting multiple segments of genomic sequences and their qualities scores into the input port over the genomic buss; storing the multiple segments of genomic sequences in the first memory; accessing and storing reference genomic data comprising a sequence of genomic data into the first memory; aligning the multiple segments of genomic sequences with the reference genomic data; locating a pointer at the first position of the reference data; (a) processing the first memory to compare individual nucleotides in the aligned multiple segments at the pointer position; processing the compared individual nucleotides to determine a culminate nucleotide from the individual nucleotides to be stored in an encoded data file at the pointer position; (b) determining if the pointer is at the last position of the reference data; if the pointer is at the last position of the reference data jumping to step (c); stepping the pointer to the next position of the reference data; returning to step (a); (c) storing the encoded data file as encoded genomic data in the second memory.

Another embodiment is a non-transitory computer readable media, comprising encoded data representing a DNA sequencing comprised of multiple DNA segments, the computer readable media produced by: inputting multiple segments of genomic sequences and their qualities scores into a computer memory; accessing reference genomic data comprising a sequence of genomic data; aligning the multiple segments with the reference genomic data; comparing individual nucleotides is the aligned multiple segments using a processor; creating a de-duplicated sequence of encoded data aligned with the reference genomic data; and storing the de-duplicated sequence on a computer storage media; wherein the encoded data contains the nucleotide label for agreed upon nucleotides at a particular nucleotide location.

BRIEF DESCRIPTION OF THE DRAWINGS

The advantages and features of the present invention will become better understood with reference to the following detailed description and claims when taken in conjunction with the accompanying drawings, in which:

DETAILED DESCRIPTION OF THE INVENTION

The presently disclosed subject matter now will be described more fully hereinafter with reference to the accompanying drawings in which one embodiment is shown. However, it should be understood that this invention may take different forms and thus the invention should not be construed as being limited to the specific embodiment set forth herein.

All documents and references referred to in this disclosure are hereby incorporated by reference for all purposes. In the figures like numbers refer to like elements throughout. Additionally, the terms "a" and "an" as used herein do not denote a limitation of quantity, but rather denote the presence of at least one of the referenced items.

Figure 2:
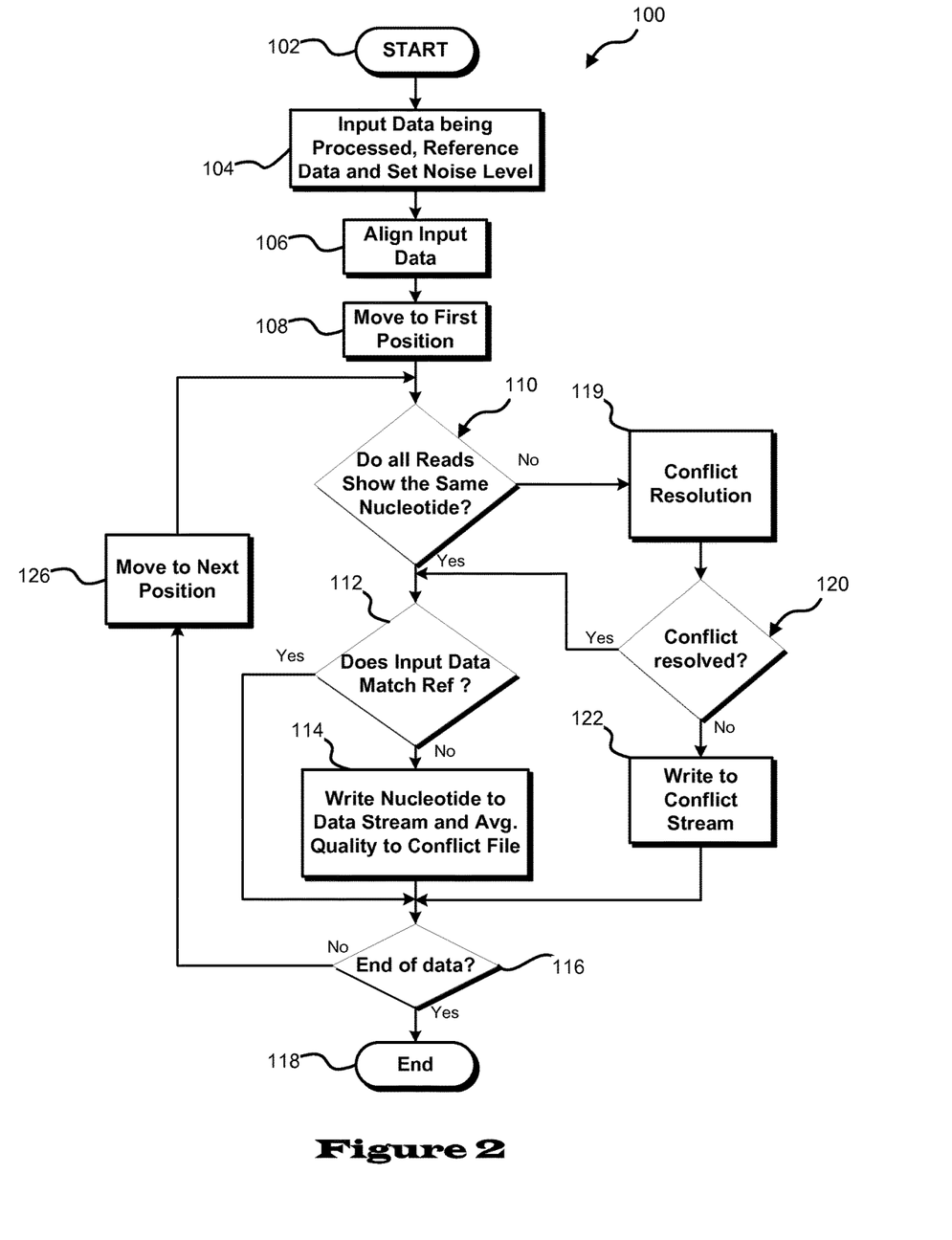
FIG. 2 is a flow chart illustrating the steps of processing input data to produce de-duplicated encoded data in accord with the present invention.
Figure 3:
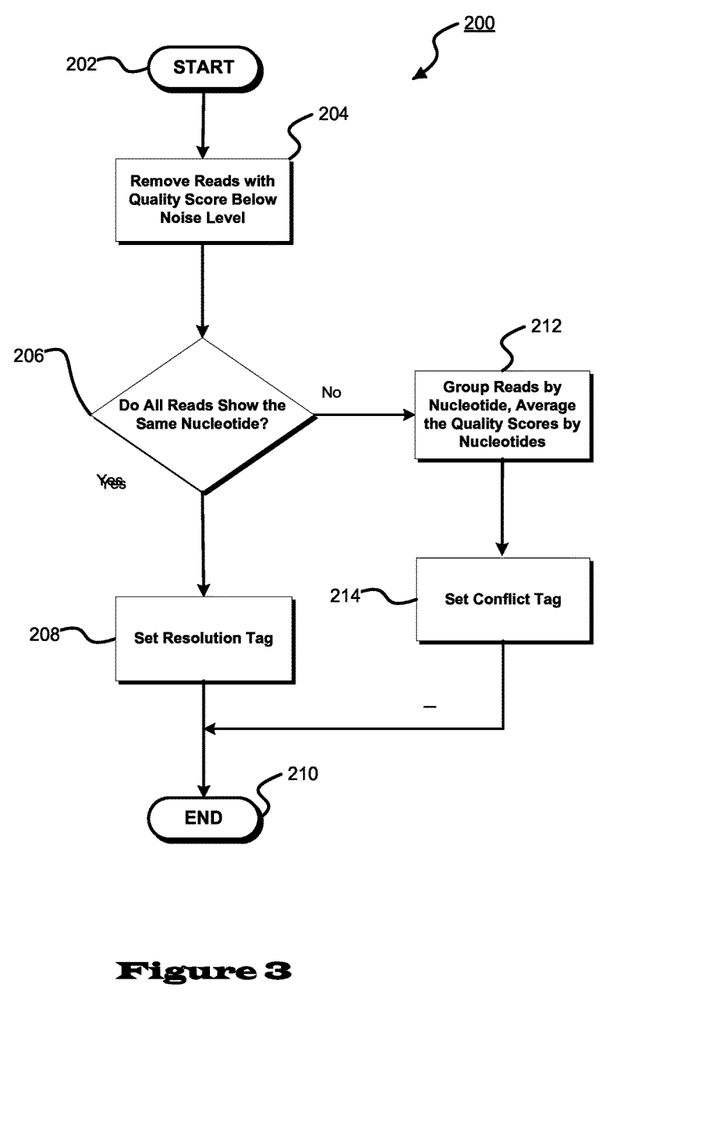
FIG. 3 is a flow chart illustrating the steps of processing nucleotide conflicts.
Figure 4:
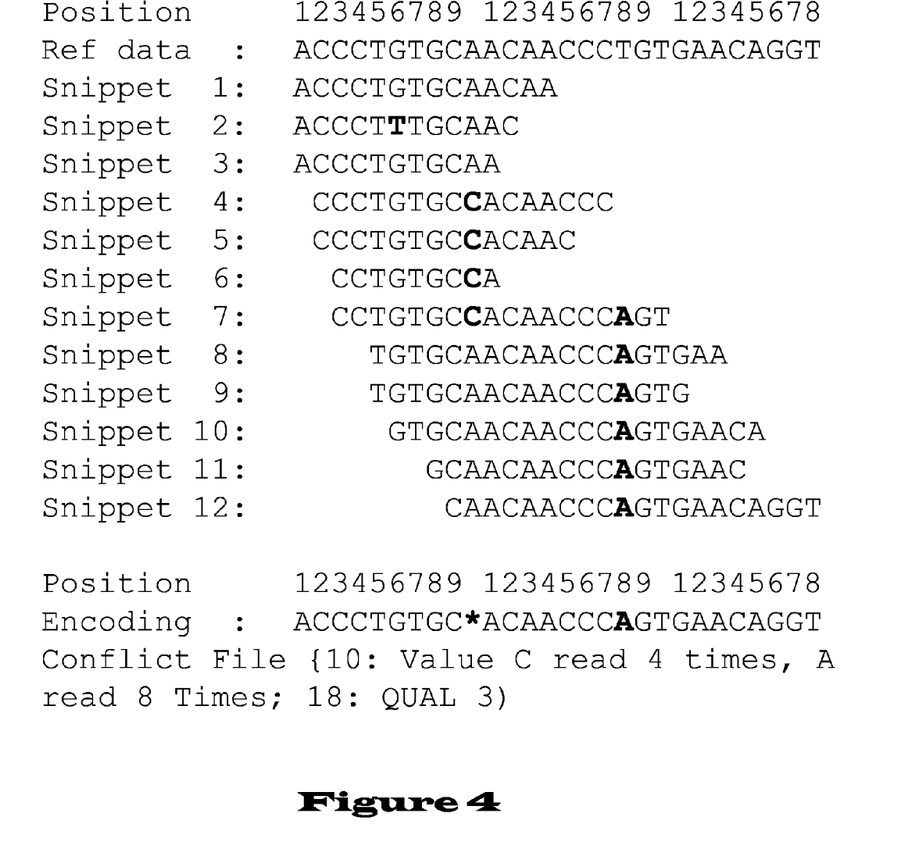
FIG. 4 illustrates the process of resolving conflicts to produce encoded data.
Figure 5:
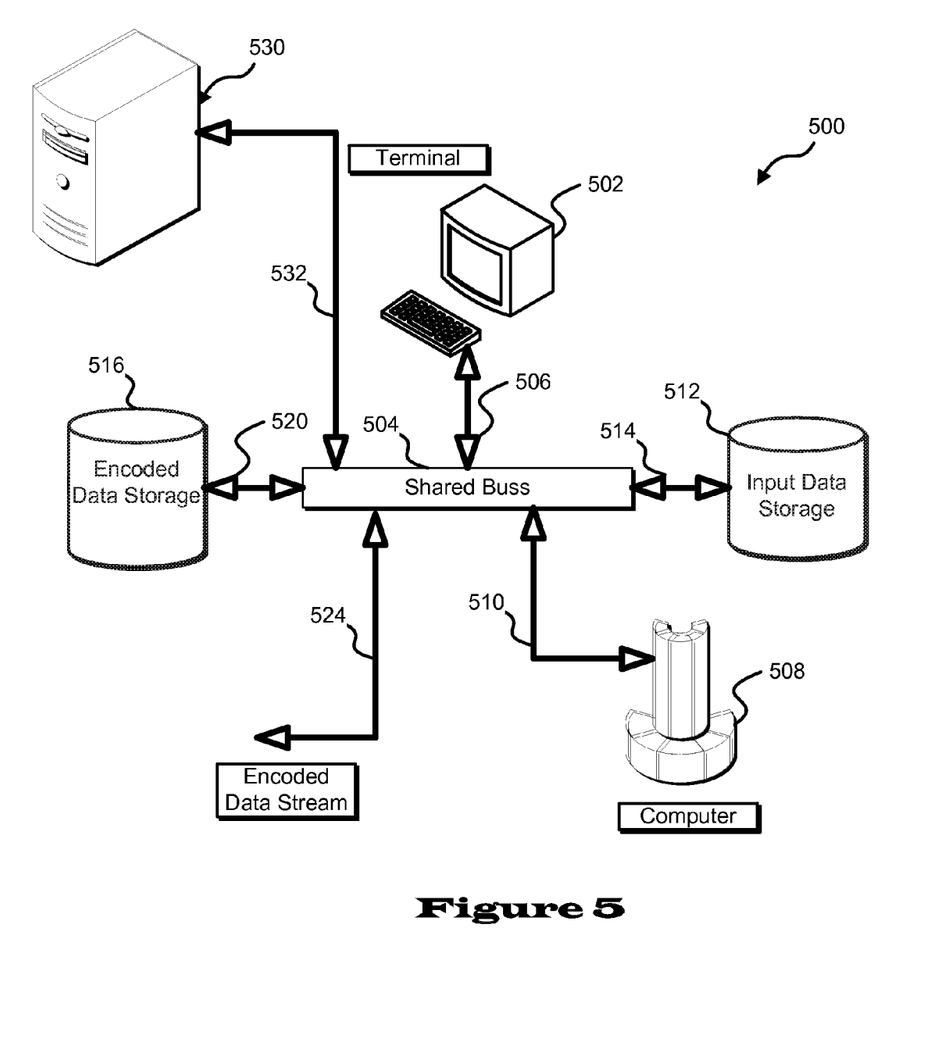
FIG. 5 shows a computerized DNA sequencing system for producing encoded data.

The present invention is explained with reference to FIGS. 1 through 5. FIG. 1 represents exemplary sequences of nucleotide data along with a reference data set; FIG. 4 illustrates the resulting encoded data of the nucleotide sequences of FIG. 1; FIGS. 2 and 3 provide flow charts for processing nucleotide data; and FIG. 5 illustrates a computerized DNA sequencing system for implementing the principles of the present invention.

The present invention is a polynucleotide (e.g., DNA or RNA) data encoding scheme that eliminates redundant genomic data, simplifies sequence alignment, and provides an auxiliary conflict file that contains information related to the encoded data. As previously provided, prior art genomic data was commonly stored in .bam or .sam file formats. Those formats include information regarding reads and re-reads of the same nucleotides obtained from different sequencing runs, along with associated quality scores and meta-data; reference snippets 1-12, QUAL data, and meta-data shown in FIG. 1, all of which in the prior art would have to be stored in a .sam or .bam file format. The result is a large amount of redundant genomic data. The principles of the present invention de-duplicate reads and re-reads of the same nucleotide, reduces those reads and re-reads into a single nucleotide, and inserts the resulting single nucleotide and an averaged QUAL score and meta-data into its proper location in an aligned encoded data stream. That encoded data stream can be stored in computer memory. In addition, information regarding de-duplication is stored in a separate conflict file; reference FIG. 4.

Turning back to FIG. 1, the present invention compares all sequenced nucleotides in all snippet (polynucleotide) segments at a particular nucleotide location relative to reference data. If the sequenced nucleotides are all the same the agreed upon nucleotide is placed in the resulting encoded data stream. This is shown in FIG. 4 where all agreed upon sequenced (e.g., culminate) nucleotides are encoded in their proper order. Specific attention is directed to position 18 wherein the agreed upon sequenced nucleotide A is stored in position A even when the reference data for position 18 is G. It is the sequenced nucleotides that control, not the reference data. Further, alignment information is contained in the encoded data so alignment information is removable, thus reducing the size of the encoded data. In addition, FIG. 1 shows the conflict file as including the information about position 18 that the nucleotide A was read 8 times.

However, if the sequenced nucleotides in all of the sequenced segments do not all agree, which is represented in FIG. 1 by nucleotides T and C highlighted in bold, data is encoded as subsequently described below after conflict resolution processing. The multiple possible values of quality nucleotides (see below) at a position are also annotated in the conflict file. Thus the conflict file can be scanned to identify possible differences between the resulting encoded data and the nucleotides found in the various snippet sequencing. Attention is drawn to nucleotide T in FIG. 4. No annotation of that nucleotide is provided as its assumed QUAL score is too low, again as subsequently explained.

The end result is that the encoded data stream contains differences between the nucleotides in the sequencing snippets following conflict resolution. The result is a tremendous reduction in data size while retaining almost all information regarding sequenced nucleotide disagreements in the conflict file. Preferably, the conflict file includes the number of reads for each nucleotide and the corresponding average quality (QUAL) for that nucleotide.

The preferred embodiment of the present invention allows a user to establish (or set) a threshold for good data which is then used to eliminate noisy or bad data from the conflict file. It is that threshold value that was used to eliminate information regarding the T nucleotide in position 6 in FIG. 4 from the conflict file. The T nucleotide was simply not good enough to be tracked.

FIG. 1 presents a flow chart for a method 100 of processing input genomic data to produce a de-duplicated encoded data stream that is in accord with the present invention. The method 100 starts, step 102, and proceeds with accepting an input sequenced data set that is to be de-deduplicate encoded, reference data, and the reference noise level threshold, step 104. The input data is aligned with the reference data, step 106. In preparation for de-duplication a computational pointer moves to the aligned first data position, step 108.

The nucleotides in the input data segments at the current (initially the first) position of the pointer are then read and a check is made to determine if all reads of the nucleotides at the current pointer position are the same, step 110. If yes, a decision is made as to whether the input data matches the reference data, step 112. If yes, a determination is then made as to whether the pointer is at the end of the input data, step 116. If not, the pointer is moved to the next position, step 126, and a return is made to step 110. These steps represent the fastest processing of the input data. All of its reads are the same, those reads match the reference data set, a high quality rating for the nucleotide exists, the reference data set nucleotide can be used in place of the input data nucleotides, and the next encoded data position is ready to be processed.

However, if in step 112 the input data nucleotides agree with each other but do not match the reference nucleotide, the input data nucleotide is written into the encoded data stream along with the averaged quality of the input nucleotides (each read would have its own quality rating) and its meta-data, step 114. This condition is shown in position 18 of FIG. 4. In addition to the input data nucleotide being input to the encoded data stream, the conflict file is populated with information regarding position 18. This is also shown in FIG. 4. Following step 114 a check is made as to whether the pointer is at the end of data, step 116. If not, the pointer is advanced to its next position, step 126 and a return is made to the start of step 110.

The immediately foregoing processing produces information in the conflict file. Since most input data base pairs should match the reference data the conflict file is relatively smaller. Given any nucleotide disagreements in the input data set a check of the conflict file provides information about those disagreements. Disagreements can be quickly and efficiently found simply by scanning the conflict file.

If it is found in step 110 that all reads and re-reads do not show the same nucleotide the process advances to step 119 for process conflict resolution. FIG. 2 shows a method 200 for handling process conflict resolution. The method 200 starts, step 202 and proceeds by removing reads with quality scores below the noise level, step 204. Step 204 prevents low quality base pair readings from contaminating the resulting encoded data stream.

After step 204 another check is made to determine if all remaining nucleotides at the current pointer position show the same nucleotide, step 206. If yes the nucleotide conflict is considered resolved and an output resolution tag is set. However, if in step 206 the remaining nucleotides do not show the same value the nucleotide reads are grouped by nucleotides and an average quality score is determined, step 212. Then a conflict tag is set, step 214.

After step 208 or step 214 one tag will be set. That tag is passed to the method 100 to either show that a conflict exists (conflict tag set) or that the nucleotide reads resolve and that no conflict exists. The method 200 ends, step 210.

Following step 210 a return is made to step 120 of the method 100 for a determination of how to proceed. If the output resolution tag is set the conflict is considered resolved and a jump is made to the start of step 112 for processing as described above and the output resolution tag is cleared for the next possible conflict. However, if the conflict tag is set, step 120 determines that the conflict is not resolved and operation passes to step 122. In step 122 information related to the conflict is added to the conflict stream. The conflict stream subsequently can be examined to determine the specific nucleotide reads that initiated the conflict. Processing is then passed to the input of step 116 for a determination as to whether the pointer for the reads just processed is at the end of the data.

The inventive encoding of the present invention enables a genomic data size reduction (by about 167), far faster data transmission rates, and improved data processing speeds. This is at least partially a result of removal of the standard genome reference.

The inventive data encoding also enables the creation and sharing of de-duplicated gene libraries by storing the encoded data in a library. This promotes file sharing by passing references to redundant data in the de-duplicated library rather than in the data itself. The encoded data not only supports the organization of de-duplicated library but also the use of nucleotides as objects, with each object of a cancer gene being part of a cancer genome atlas (TCGA).

The inventive genomic data encoding also supports efficient, searchable compression of de-duplicated Genomic Data. In practice the present invention enables a tremendous reduction in the required size of stored genomic data by exploiting the rather limited genomic variations among humans (0.1%). The reduction in size reduces the genomic data storage footprint and the bandwidth required to transport genomic data. Instead of the 39 exabytes required in the prior art to store the whole genome sequences for every person mentioned in the background genomic de-duplication shrinks the genome sequences to under 1 PB.

Turning now to FIG. 5, the actual production of encoded data is a task well suited to a computerized environment. Such a computerized environment may be part of a DNA sequencing system 500. Such a DNA sequencing system 500 may include a terminal 502 that communicates with other elements (discussed subsequently) that are connected to a shared buss 504. The terminal 502 is connected to the shared buss 504 by a bi-directional local buss 506. The terminal 502 communicates as required with a computer 508 which is connected to the shared buss 504 by a computer buss 510. The computer 508 runs the methods 100 and 200 illustrated in FIGS. 2 and 3. Input data which includes reference data, QUAL data, and meta-data as exemplary illustrated in FIG. 1, is produced by a DNA sequencer 530 which is connected to the shared buss 504 via a local sequencer buss 532. That Input data can be stored in input data storage 512. The input data is applied to the computer 508 as required over the shared buss 504 and along a local input data bus 514.

The computer 508 processes the input data to produce encoded data, exemplary illustrated in FIG. 4. That encoded data can be transmitted over the computer bus 510, along the shared buss 504 to encoded data storage 516 via encoded data storage buss 520. Alternatively, the encoded data can be streamed out over an encoded data stream buss 524.

The terminal 502 initiates running the method 100, may operate the DNA sequencer 530, and may control the overall operation and output human readable information. Following software commands the computer 508 runs the methods 100 and 200 using its processor.

It is to be understood that while the figures and the above description illustrate the present invention, they are exemplary only. They are not intended to be exhaustive or to limit the invention to the precise forms disclosed, and obviously many modifications and variations are possible in light of the above teaching. Others who are skilled in the applicable arts will recognize numerous modifications and adaptations of the illustrated embodiments that remain within the principles of the present invention. Therefore, the present invention is to be limited only by the appended claims.

Publications that may be relevant to the present invention include the following which are hereby incorporated by reference for all purposes:

Avani Wildani, Ian Adams, Ethan L. Miller, Single-Snapshot File System Analysis, Proceedings of the 21st IEEE International Symposium on Modeling, Analysis, and Simulation of Computer and Telecommunication Systems (MASCOTS 2013), August 2013. [Prediction and Grouping].

Ian Adams, Mark W. Storer, Avani Wildani, Ethan L. Miller, Brian Madden, Validating Storage System Instrumentation, Proceedings of the 21st IEEE International Symposium on Modeling, Analysis, and Simulation of Computer and Telecommunication Systems (MASCOTS 2013), August 2013. [Archival Storage] [Tracing and Benchmarking].

Aleatha Parker-Wood, Brian Madden, Michael McThrow, Darrell D. E. Long, Ian Adams, Avani Wildani, Examining Extended and Scientific Metadata for Scalable Index Designs, Proceedings of the 6th International Systems and Storage Conference (SYSTOR 2013), June 2013. [Scalable File System Indexing] [Dynamic Non-Hierarchical File Systems].

Yangwook Kang, Yang-suk Kee, Ethan L. Miller, Chanik Park, Enabling Cost-effective Data Processing with Smart SSD, the 29th IEEE Symposium on Massive Storage Systems and Technologies (MSST 13), May 2013. [Storage Class Memories].

Hsu-Wan Kao, Jehan-Francois Paris, Darrell D. E. Long, Thomas Schwarz, A Flexible Simulation Tool for Estimating Data Loss Risks in Storage Arrays, 29th IEEE Symposium on Massive Storage Systems and Technologies, May 2013. [Archival Storage] [Reliable Storage].

Avani Wildani, Ethan L. Miller, Ohad Rodeh, HANDS: A Heuristically Arranged Non-Backup In-line Deduplication System, Proceedings of the 29th IEEE International Conference on Data Engineering (ICDE 2013), April 2013. [Deduplication] [Prediction and Grouping].

Yan Li, Nakul Dhotre, Yasuhiro Ohara, Thomas Kroeger, Ethan L. Miller, Darrell D. E. Long, Horns: Fine-Grained Encryption-Based Security for Large-Scale Storage, Proceedings of the 11th Conference on File and Storage Systems (FAST 2013), February 2013. [Secure File and Storage Systems] [Ultra-Large Scale Storage].

James Plank, Kevin Greenan, Ethan L. Miller, Screaming Fast Galois Field Arithmetic Using Intel SIMD Extensions, Proceedings of the 11th Conference on File and Storage Systems (FAST 2013), February 2013.

Thomas Schwarz, Ignacio Corderi, Darrell D. E. Long, Jehan-Francois Paris, Simple, Exact Placement of Data in Containers, Proceedings of the International Conference on Computing, Networking and Communications (ICNC), January 2013. [Scalable File System Indexing] [Dynamic Non-Hierarchical File Systems]

Rekha Pitchumani, Andy Hospodor, Ahmed Amer, Yangwook Kang, Ethan L. Miller, Darrell D. E. Long, Emulating a Shingled Write Disk, Proceedings of the 20th IEEE International Symposium on Modeling, Analysis, and Simulation of Computer and Telecommunication Systems (MASCOTS 2012), August 2012. [Shingled Disk].

Ziqian Wan, Alex Nelson, Tao Li, Darrell D. E. Long, Andy Hospodor, Computer Hard Drive Geolocation by HTTP Feature Extraction, Technical Report UCSC-SSRC-12-04, May 2012. Technical Report UCSC-S SRC-12-04 [Digital Forensics].

Thomas Schwarz, Qin Xin, Ethan L. Miller, Darrell D. E. Long, Andy Hospodor, Spencer Ng, Disk Scrubbing in Large Archival Storage Systems, Proceedings of the 12th International Symposium on Modeling, Analysis, and Simulation of Computer and Telecommunication Systems (MASCOTS '04), October 2004, pages 409-418. Won Best Paper award. [Archival Storage] [Reliable Storage] [Ultra-Large Scale Storage].

Andy Hospodor, Ethan L. Miller, Interconnection Architectures for Petabyte-Scale High-Performance Storage Systems, Proceedings of the 21st IEEE/12th NASA Goddard Conference on Mass Storage Systems and Technologies, April 2004, pages 273-281. [Ultra-Large Scale Storage].

Ewing B, Hillier L, Wendl M C, Green P (1998). "Base-calling of automated sequencer traces using phred. I. Accuracy assessment". Genome Res. 8 (3): 175-185.

Ewing, Green (1998). "Base-calling of automated sequencer traces using phred. II. Error probabilities". Genome Res. 8 (3): 186-194. doi:10.1101/gr.8.3.186. PMID 9521922.

Dear S, Staden R (1992). "A standard file format for data from DNA sequencing instruments". DNA Seq. 3 (2): 107-110. doi:10.3109/10425179209034003. PMID 1457811.

Bonfield J K, Staden R (25 Apr. 1995). "The application of numerical estimates of base calling accuracy to DNA sequencing projects". Nucleic Acids Res. 23 (8): 1406-1410. doi:10.1093/nar/23.8.1406. PMC 306869.PMID 7753633.

Churchill G A, Waterman M S (September 1992). "The accuracy of DNA sequences: estimating sequence quality". Genomics 14 (1): 89-98. doi:10.1016/S0888-7543(05) 80288-5. PMID 1358801; Genome Biology 2011, 12:R112.

E. Green 1998 "Base-calling of automated sequencer traces using phred. II. Error probabilities"; Genome Research 8: 186-194.

The present invention may be defined, but not limited, by the following claims.

The invention claimed is:

1. A method for compressing genomic data, the method comprising the steps of:
   (i) providing a computer having a memory in functional communication with a processor;
   (ii) inputting multiple segments of genomic sequences and their quality scores into the memory;
   (iii) providing reference genomic data comprising a sequence of genomic data;
   (iv) accessing the reference genomic data;
   (v) aligning the multiple segments with the reference genomic data;
   (vi) comparing individual nucleotides in the aligned multiple segments using the processor;
   (vii) creating a de-duplicated sequence of encoded data aligned with the reference genomic data; and
   (viii) creating a conflict file during de-duplication, the conflict file containing information regarding conflicts in the aligned multiple segments,
   wherein the encoded data contains nucleotide labels for agreed upon nucleotides at a particular nucleotide location.

2. The method according to claim 1, further including the step of placing a quality score threshold in the memory.

3. The method according to claim 2, further including the step of ignoring a nucleotide in the aligned multiple segments having a quality below the threshold.

4. The method according to claim 3, further including the step of selecting a nucleotide from conflicting nucleotides and inserting the selected nucleotide in the encoded data and inserting information regarding the conflicting nucleotides in the conflict file.

5. A computer having a processor, a first memory, a second memory and an input port programmed to produce encoded genomic data, by performing the following steps:
   inputting multiple segments of genomic sequences and their qualities scores into the input port;
   storing the multiple segments of genomic sequences in the first memory;
   accessing and storing reference genomic data comprising a sequence of genomic data into the first memory;
   aligning the multiple segments of genomic sequences with the reference genomic data;
   locating a pointer at a first position of the reference data;
   (a) processing the first memory to compare individual nucleotides in the aligned multiple segments at the pointer position;
   processing the compared individual nucleotides to determine a culminate nucleotide from the individual nucleotides to be stored in an encoded data file at the pointer position;
   (b) determining if the pointer is at the last position of the reference data;
   if the pointer is at the last position of the reference data jumping to step (c);
   stepping the pointer to a subsequent position of the reference data;
   returning to step (a); and
   (c) storing the encoded data file as encoded genomic data in the second memory.

6. The computer according to claim 5, further including the step of creating a conflict file in said second memory for containing information regarding conflicts in aligned nucleotides.

7. The computer according to claim 6, further including the step of storing a quality score threshold in the first memory.

8. The computer according to claim 7, further including the step of ignoring a nucleotide in an aligned multiple segment that has a quality below the threshold.

9. A genomic sequencing system, comprising:
   a genomic sequencer for producing segments of DNA sequences having QUAL scores and meta-data;
   a computer having a processor, a first memory, a second memory, and an input port;
   a genomic bus connecting said genomic sequencer to said input port;
   wherein the computer interacts with the genomic sequencer to perform the following steps:
   inputting multiple segments of genomic sequences and their qualities scores into the input port over the genomic bus;
   storing the multiple segments of genomic sequences in the first memory;
   accessing and storing reference genomic data comprising a sequence of genomic data into the first memory;
   aligning the multiple segments of genomic sequences with the reference genomic data;
   locating a pointer at a first position of the reference data;
   (a) processing the first memory to compare individual nucleotides in the aligned multiple segments at the pointer position; processing the compared individual nucleotides to determine a culminate nucleotide from the individual nucleotides to be stored in an encoded data file at the pointer position;
   (b) determining if the pointer is at the last position of the reference data;
   if the pointer is at the last position of the reference data jumping to step (c);
   stepping the pointer to a subsequent position of the reference data;
   returning to step (a); and
   (c) storing the encoded data file as encoded genomic data in the second memory.

10. The genomic sequencing system according to claim 9, further including the step of creating a conflict file in said second memory containing information regarding conflicts in aligned nucleotides.

11. The genomic sequencing system according to claim 10, further including the step of storing a quality score threshold in the first memory and the step of ignoring a nucleotide in an aligned multiple segment that has a quality below the threshold.

12. A non-transitory computer readable media, comprising encoded data representing a DNA sequencing comprised of multiple DNA segments, the computer readable media produced by:
inputting multiple segments of genomic sequences and their qualities scores into a computer memory;
accessing reference genomic data comprising a sequence of genomic data;
aligning the multiple segments with the reference genomic data;
comparing individual nucleotides in the aligned multiple segments using a processor;
creating a de-duplicated sequence of encoded data aligned with the reference genomic data;
storing the de-duplicated sequence on a computer storage media; and
creating a conflict file during de-duplication, the conflict file containing information regarding conflicts in aligned nucleotides,
wherein the encoded data contains nucleotide labels for culminate nucleotides at a particular nucleotide location.

13. The non-transitory computer readable media according to claim 12, wherein the encoded data is produced by removing nucleotides from the segments of genomic sequences when the nucleotide has a quality score below the threshold.

14. The non-transitory computer readable media according to claim 13, wherein the encoded data is produced by selecting a nucleotide from conflicting nucleotides and inserting the selected nucleotide in the encoded data and inserting information regarding the conflicting nucleotides in the conflict file.

* * * * *

SEQUENCE LISTING

```
<160> NUMBER OF SEQ ID NOS: 13

<210> SEQ ID NO 1
<211> LENGTH: 28
<212> TYPE: DNA
```

```
<213> ORGANISM: Artificial Sequence
<220> FEATURE:
<223> OTHER INFORMATION: Sequence is solely illustrative of the
      invention

<400> SEQUENCE: 1
accctgtgca acaaccctgt gaacaggt                                              28

<210> SEQ ID NO 2
<211> LENGTH: 14
<212> TYPE: DNA
<213> ORGANISM: Artificial Sequence
<220> FEATURE:
<223> OTHER INFORMATION: Sequence is solely illustrative of the
      invention

<400> SEQUENCE: 2
accctgtgca acaa                                                             14

<210> SEQ ID NO 3
<211> LENGTH: 12
<212> TYPE: DNA
<213> ORGANISM: Artificial Sequence
<220> FEATURE:
<223> OTHER INFORMATION: Sequence is solely illustrative of the
      invention

<400> SEQUENCE: 3 acccttt gca ac                                                              12

<210> SEQ ID NO 4
<211> LENGTH: 11
<212> TYPE: DNA
<213> ORGANISM: Artificial Sequence
<220> FEATURE:
<223> OTHER INFORMATION: Sequence is solely illustrative of the
      invention

<400> SEQUENCE: 4
accctgtgca a                                                                11

<210> SEQ ID NO 5
<211> LENGTH: 16
<212> TYPE: DNA
<213> ORGANISM: Artificial Sequence
<220> FEATURE:
<223> OTHER INFORMATION: Sequence is solely illustrative of the
      invention

<400> SEQUENCE: 5
ccctgtgcca caaccc                                                           16

<210> SEQ ID NO 6
<211> LENGTH: 14
<212> TYPE: DNA
<213> ORGANISM: Artificial Sequence
<220> FEATURE:
<223> OTHER INFORMATION: Sequence is solely illustrative of the
      invention

<400> SEQUENCE: 6
ccctgtgcca caac                                                             14

<210> SEQ ID NO 7
<211> LENGTH: 18
<212> TYPE: DNA
<213> ORGANISM: Artificial Sequence
```

```
<220> FEATURE:
<223> OTHER INFORMATION: Sequence is solely illustrative of the
      invention

<400> SEQUENCE: 7
cctgtgccac aacccagt                                                       18

<210> SEQ ID NO 8
<211> LENGTH: 19
<212> TYPE: DNA
<213> ORGANISM: Artificial Sequence
<220> FEATURE:
<223> OTHER INFORMATION: Sequence is solely illustrative of the
      invention

<400> SEQUENCE: 8
tgtgcaacaa cccagtgaa                                                      19

<210> SEQ ID NO 9
<211> LENGTH: 17
<212> TYPE: DNA
<213> ORGANISM: Artificial Sequence
<220> FEATURE:
<223> OTHER INFORMATION: Sequence is solely illustrative of the
      invention

<400> SEQUENCE: 9
tgtgcaacaa cccagtg                                                        17

<210> SEQ ID NO 10
<211> LENGTH: 20
<212> TYPE: DNA
<213> ORGANISM: Artificial Sequence
<220> FEATURE:
<223> OTHER INFORMATION: Sequence is solely illustrative of the
      invention

<400> SEQUENCE: 10
gtgcaacaac ccagtgaaca                                                     20

<210> SEQ ID NO 11
<211> LENGTH: 17
<212> TYPE: DNA
<213> ORGANISM: Artificial Sequence
<220> FEATURE:
<223> OTHER INFORMATION: Sequence is solely illustrative of the
      invention

<400> SEQUENCE: 11
gcaacaaccc agtgaac                                                        17

<210> SEQ ID NO 12
<211> LENGTH: 20
<212> TYPE: DNA
<213> ORGANISM: Artificial Sequence
<220> FEATURE:
<223> OTHER INFORMATION: Sequence is solely illustrative of the
      invention

<400> SEQUENCE: 12
caacaaccca gtgaacaggt                                                     20

<210> SEQ ID NO 13
<211> LENGTH: 28
<212> TYPE: DNA
<213> ORGANISM: Artificial Sequence
<220> FEATURE:
```

```
<223> OTHER INFORMATION: Sequence is solely illustrative of the
      invention
<220> FEATURE:
<221> NAME/KEY: misc_feature
<222> LOCATION: (10)..(10)
<223> OTHER INFORMATION: n is a, c, g, or t

<400> SEQUENCE: 13
accctgtgcn acaacccagt gaacaggt                                          28
```